United States Patent [19]

Chang et al.

[11] Patent Number: 5,508,440
[45] Date of Patent: Apr. 16, 1996

[54] HYDROXYMETHYLPOLYTHIOPHENE DERIVATIVES

[75] Inventors: Ching-Te Chang; Chen-Tao Lee, both of Taipei; Fueng-Lan Lin, Hsinchu, all of Taiwan

[73] Assignee: Industrial Technology Research Institute, Hsinchu, Taiwan

[21] Appl. No.: 71,695

[22] Filed: Jun. 4, 1993

[51] Int. Cl.$^6$ .......................... C07D 409/04; A61K 31/38
[52] U.S. Cl. ................................. 549/59; 549/60
[58] Field of Search ................. 549/60, 59, 70, 549/78, 399, 414; 514/460, 444

[56] References Cited

U.S. PATENT DOCUMENTS

| | | | |
|---|---|---|---|
| 3,050,442 | 8/1962 | Bijloo et al. | 549/59 |
| 3,086,854 | 4/1963 | Harvey, Jr. | 549/68 |
| 4,645,777 | 2/1987 | Burkart et al. | 514/444 |
| 4,749,712 | 6/1988 | Haber | 514/438 |
| 4,937,256 | 6/1990 | Kober et al. | 514/444 |
| 4,939,165 | 7/1990 | Burkart et al. | 514/444 |
| 5,045,563 | 9/1991 | Morand et al. | 514/444 |
| 5,180,838 | 1/1993 | Morand et al. | 549/59 |

OTHER PUBLICATIONS

Chemical Abstract No. CA101(13):110662d of Nukleofilinge Reakts. Karbonil'nykh Soedin., 34–5, Shklyaev et al, (1982).

Mac Eachern et al, "Synethesis and characterization of Alkyl—, Halo— and Hetero-substituted-α-Terthienyls", Tetrahedron, vol. 44. No. 9 pp. 2403–2412 (1988).

Hudson et al, "Photoactive Antiviral and Cytotoxic . . . Throphenes . . . ", Chemosphere, vol. 19, Nos. 8/9, pp. 1329–1343, (1989).

Marles et al, "Structure–Activity Studies of Photoactivated . . . Throphemes", Photochemistry and Photobiology, vol. 56, No. 4. pp. 479–487, (1992).

Wiklund et al, Stereochemistry of 3',3'—Thienyls, Chemica Scripta (1974) 6, 137–144.

Chemical Abstract, No. 89:215253 of Journal Heterocycl. Chem., 15(4), 593–9, (1978).

Matsomoto, Yasuo, et al., Kogyo Kagaku Zasshi, (Japan) 62: 1559 (1959).

Winter, Charles A., et al. Biol. Med., 111: 544 (1962).

Roszkowski, Adolph P. et al., J. Pharmacol. Exp. Ther., 179: 114 (1971).

J. Kagan, "Naturally Occurring Di— and Trithiophenes", 1991, Prog. Chem. Org. National Prod., vol. 56, pp. 88–169.

Primary Examiner—Allen J. Robinson
Assistant Examiner—Deborah Lambkin
Attorney, Agent, or Firm—Fish & Richardson

[57] ABSTRACT

Novel hydroxymethylthiophene derivatives and their medical use in treating or preventing inflammation and edema.

6 Claims, No Drawings

HYDROXYMETHYLPOLYTHIOPHENE DERIVATIVES

BACKGROUND OF THE INVENTION

This invention relates to hydroxymethylpolythiophene derivatives and their medical use.

Recent chemical and pharmacological activity studies on the extract of the Compositae Chinese herbs demonstrate that their unique chemical components of hydroxymethylpolythiophene derivatives possess useful functions, such as anti-edema, anti-inflammatory, interferon-inducing, immunomodulating and anti-cancer activities.

No pharmacological activities of hydroxymethylpolythiophene or derivatives thereof have hitherto been reported.

SUMMARY OF THE INVENTION

One aspect of the present invention relates to a compound of the formula:

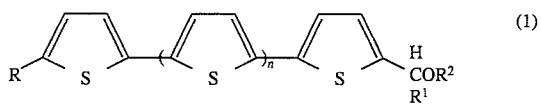

(1)

in which n is 0; R is —$CH_2OR^2$, —$CH(R^1).OR^2$, —$CH(O—Z)_2$, or —$COR^3$; $R^1$ is $C_{1-6}$ alkyl, $C_{2-6}$ alkenyl, $C_{1-6}$ alkoxy, or $C_{1-6}$ acyloxy; $R^2$ is H, $C_{1-6}$ alkyl, $C_{2-6}$ alkenyl, $C_{1-6}$ hydroxyalkyl, $C_{2-6}$ alkoxyalkyl, tetrahydropyranyl, $C_{1-6}$ acyl, —CO—Y—COOH; and $R^3$ is H, $C_{1-6}$ alkyl, $C_{2-6}$ alkenyl, or $C_{1-6}$ alkoxy; wherein Z is $C_{1-6}$ alkyl, $C_{2-6}$ alkenyl, or $C_{1-6}$ acyl; and Y is $C_{1-6}$ alkylidene, $C_{2-6}$ alkenylidene, or phenylene. Preferably, R is —$CH_2OR^2$, —$CH(R^1).OR^2$, or —$COR^3$; $R^1$ is $C_{1-6}$ alkyl; $R^2$ is H, $C_{1-6}$ acyl, or —CO—Y—COOH; and Y is —$CH_2$—$CH_2$—, —CH=CH—, or phenylene.

Another aspect of this invention is a compound of formula (1), in which n is 0; R is —$CH(R^1)OCH_3$, —$CH(R^1).OR^2$, —$CH(O—Z)_2$, or —$COR^3$; $R^1$ is H, $C_{1-6}$ alkyl, $C_{2-6}$ alkenyl, $C_{1-6}$ alkoxy, or $C_{1-6}$ acyloxy; $R^2$ is H, $C_{2-6}$ alkyl, $C_{2-6}$ alkenyl, $C_{1-6}$ hydroxyalkyl, $C_{2-6}$ alkoxyalkyl, tetrahydropyranyl, $C_{1-6}$ acyl, —CO—Y—COOH; and $R^3$ is H, $C_{1-6}$ alkyl, $C_{2-6}$ alkenyl, or $C_{1-6}$ alkoxy; wherein Z is $C_{1-6}$ alkyl, $C_{2-6}$ alkenyl, or $C_{1-6}$ acyl; and Y is $C_{1-6}$ alkylidene, $C_{2-6}$ alkenylidene, or phenylene. Preferably, R is —$CH(R^1).OR^2$ or —$COR^3$; $R^1$ is H; $R^2$ is H, $C_{1-6}$ acyl, or —CO—Y—COOH; and Y is —$CH_2$—$CH_2$—, —CH=CH—, or phenylene.

Also within the invention is a compound of formula (1), in which n is 1 or 2; R is —$CH(R^1).OR^2$, —$CH(O—Z)_2$, or —$COR^3$; $R^1$ is H, $C_{1-6}$ alkyl, $C_{2-6}$ alkenyl, $C_{1-6}$ alkoxy, or $C_{1-6}$ acyloxy; $R^2$ is H, $C_{1-6}$ alkyl, $C_{2-6}$ alkenyl, $C_{1-6}$ hydroxyalkyl, $C_{2-6}$ alkoxyalkyl, tetrahydropyranyl, $C_{1-6}$ acyl, —CO—Y—COOH; and $R^3$ is H, $C_{1-6}$ alkyl, $C_{2-6}$ alkenyl, or $C_{1-6}$ alkoxy; wherein Z is $C_{1-6}$ alkyl, $C_{2-6}$ alkenyl, or $C_{1-6}$ acyl; and Y is $C_{1-6}$ alkylidene, $C_{2-6}$ alkenylidene, or phenylene. Preferably, n is 1; R is —$CH(R^1).OR^2$ or —$COR^3$; $R^1$ is H; $R^2$ is H, $C_{1-6}$ acyl, or —CO—Y—COOH; and Y is —$CH_2$—$CH_2$—, —CH=CH—, or phenylene.

$C_{1-6}$ hydroxyalkyl and $C_{1-6}$ akoxyalkyl refer to $C_{1-6}$ alkyl groups substituted with a hydroxyl functionality and an alkoxy functionality, respectively, e.g., —$CH_2CH_2OH$ and —$CH_2CH_{20}CH_3$. Examples of $C_{1-6}$ acyloxy include, but are not limited to, $CH_3.CO.O$— and $CH_3(CH_2)_4.CO—O$—.

The term "alkyl", "alkenyl" or the alkyl or alkenyl moiety of a substituted or a divalent alkyl or alkenyl group (e.g., hydroxyalkyl, alkoxy or alkenylidene) refers to both straight and branched carbon skeletons.

The term "phenylene" refers to p-, o- and m-phenylene. As an example, p-phenylene has the structure of

The term "alkylidene" refers to a divalent radical which has two hydrogens fewer than the alkane. Examples of $C_{1-6}$ alkylidene include, but are not limited to, $CH_3$—$CH_2$= and —$CH_2$—$CH_2$—. Similarly, examples of $C_{1-6}$ alkenylidene include, but are not limited to, —CH=CH— and —$CH_2CH$=$CHCH_2$—.

Set forth below are examples of compounds of this invention. (Me stands for methyl and Et for ethyl.)

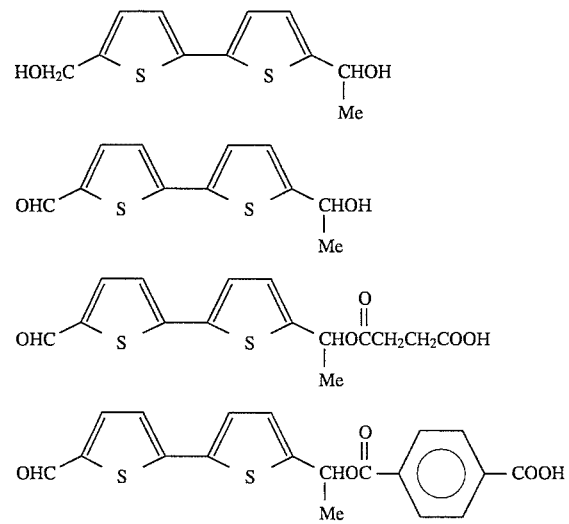

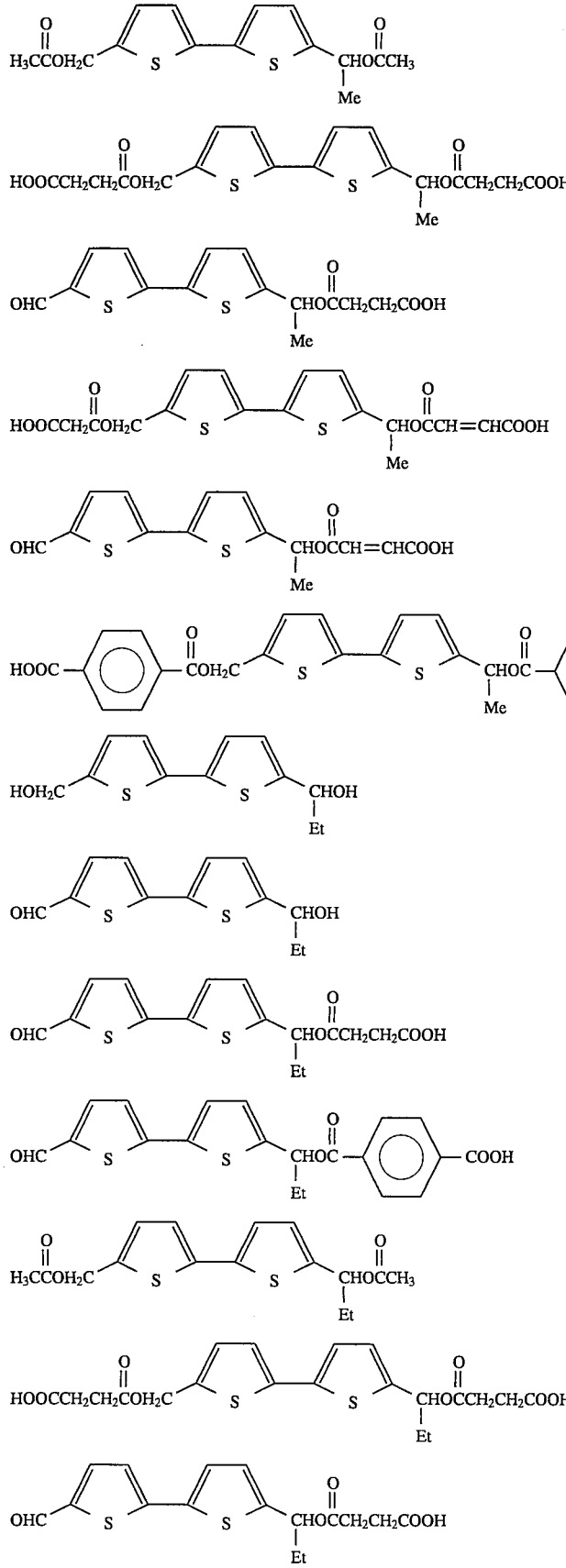

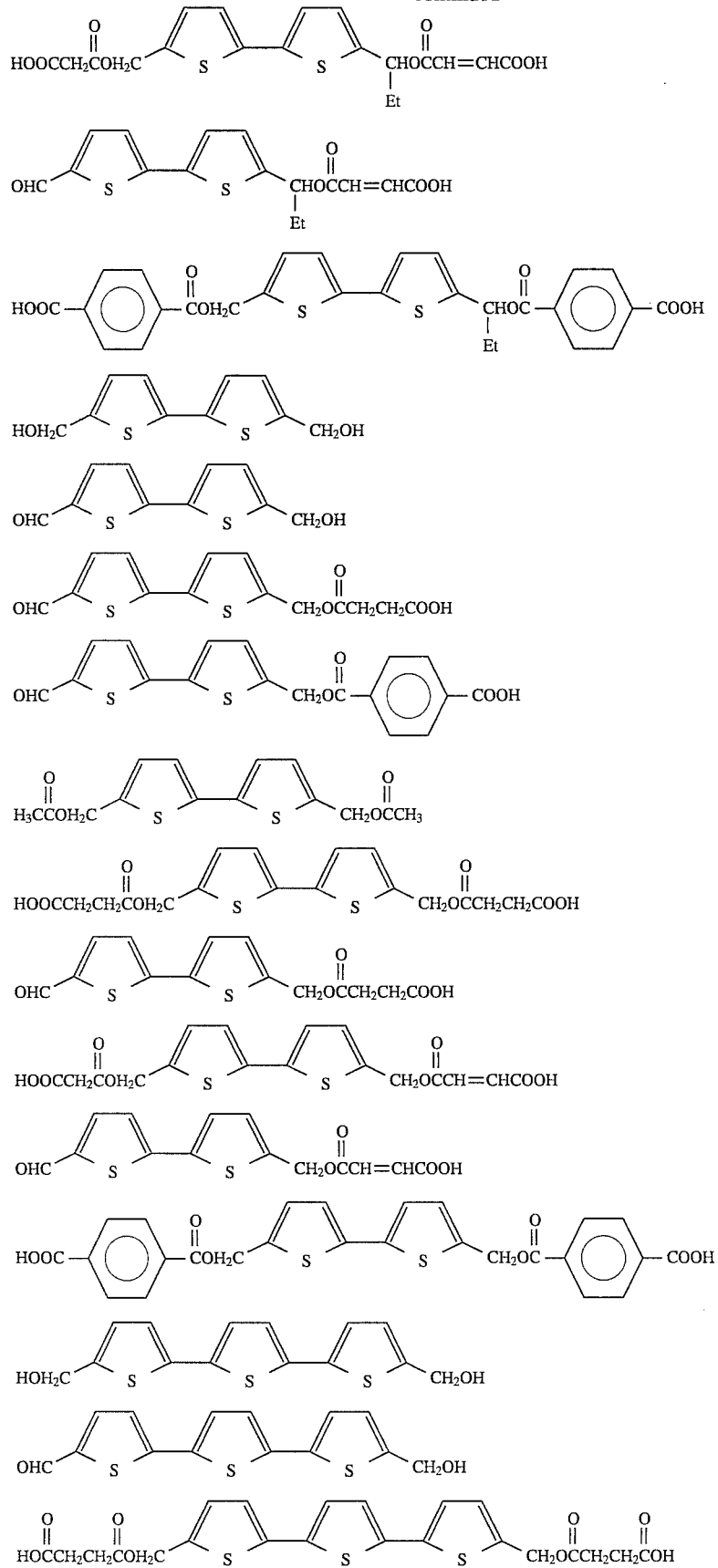

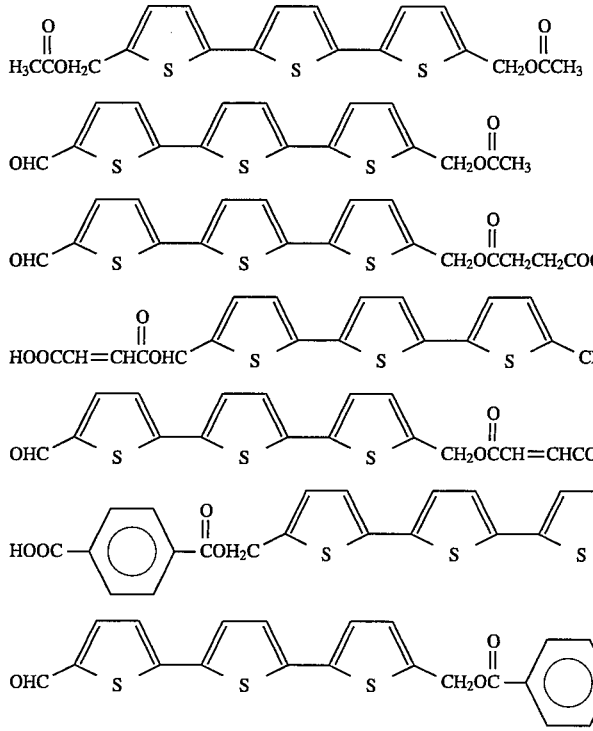

Note that a salt or an ester of any of the above-described compounds is also within the scope of this invention.

Other features and advantages of the present invention will be apparent from the following drawings and description of the preferred embodiments, and also from the appending claims.

DESCRIPTION OF THE PREFERRED EMBODIMENTS

CHEMICAL SYNTHESIS

The following synthetic methods, i.e., A through J, can be applied for the preparation of hydroxymethyl-polythiophene derivatives of this invention. Note that symbols n, R, $R^1$, $R^3$ and $R^2$ have been defined above. New symbols (e.g., m or X) are defined when they first appear, and defined again to promote clarity whenever necessary.

A. As shown in the following reaction, $\alpha$, $\alpha'''$-diacyl polythiophene derivatives (e.g., $\alpha$, $\alpha'''$-diformyl polythiophene) can be readily reduced to form $\alpha$, $\alpha'''$-dihydroxymethyl polythiophene derivative.

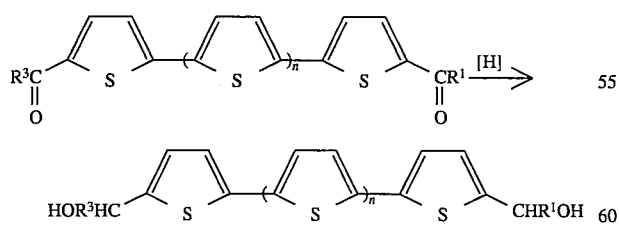

B. As shown in the following reaction, $\alpha$-alkylhydroxymethyl-$\alpha'''$-alkoxymethyl polythiophene derivatives can be obtained by the reduction $\alpha$-acyl-$\alpha'''$-alkoxymethyl polythiophene.

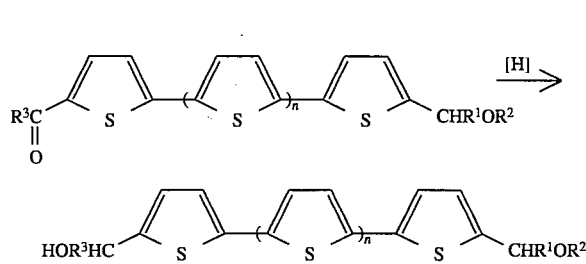

C. As shown in the following reaction, $\alpha$, $\alpha'''$-dialkylhydoxymethyl polythiophene derivatives can be obtained by the Grignard reaction.

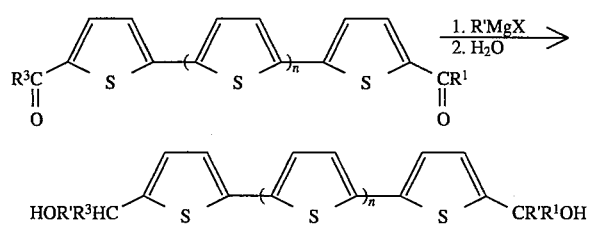

wherein $R'=R^1$ or $R^3$.

D. As shown in the following reaction, $\alpha$-alkyl hydroxymethyl-$\alpha'''$-alkoxymethyl polythiophene derivatives can also be obtained by the Grignard reaction.

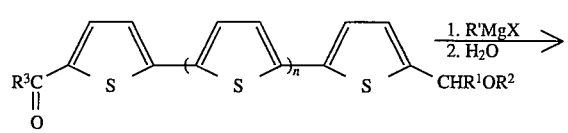

-continued

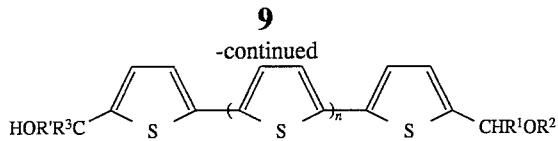

E. As shown in the following reaction, symmetric α, α'''-dialkoxymethyl polythiophene derivatives can be obtained by the Ullmann coupling reaction.

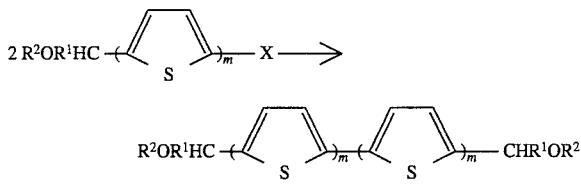

wherein m=1 or 2; and X=Br or I.

F. As shown in the following reaction, symmetric α, α'''-dialkoxy polythiophene derivatives can be obtained by the condensation of alkoxymethyl polythiophene under the catalysis of a palladium, nickel or copper salt derivative.

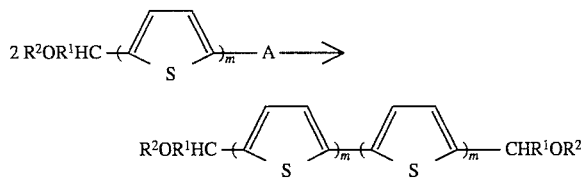

wherein A=H, Br, I or Li.

G. As shown in the following reaction, α, α'''-dialkoxymethyl or α-monoalkoxymethyl-α'''-monocarbonyl polythiophene derivatives can be obtained by the condensation of the lithium, magnesium, tin or zinc salt of α-alkoxymethyl polythiophene or α-monocarbony polythiophene derivative under the catalysis of a palladium, nickel or copper salt derivative.

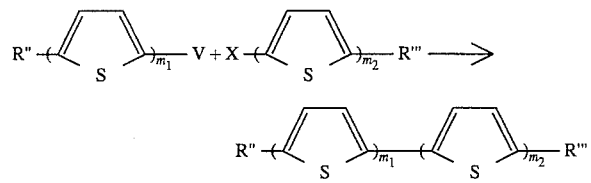

wherein each of $m^1$ and $m^2$=1 or 2;
R", R'''=—$CHR^1OR^2$ or —$COR^3$;
V=MgX, Li, $Sn(R°)_3$, or ZnX;
X=Cl, Br, or I; and
R°=$C_{1-4}$ alkyl.

H. As shown in the following reaction, symmetric α, α'''-dialkoxymethyl polythiophene derivatives can be obtained by the Grignard condensation of a dihalopolythiophene and lithium, magnesium, tin or zinc derivative of α-alkoxymethyl thiophene under the catalysis of a palladium, nickel or copper salt derivative.

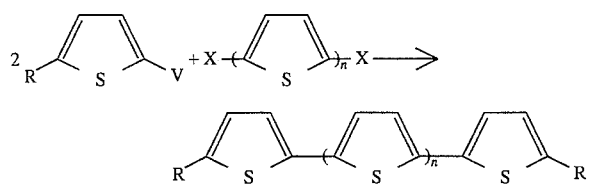

wherein V=MgX, Li, $Sn(R°)_3$, or ZnX;
X=Cl, Br, or I; and
R°=$C_{1-4}$ alkyl.

I. As shown in the following reaction, α-alkoxymethyl or α-hydroxymethyl-α'''-formyl polythiophene derivative can be obtained by the formylation of a α-hydroxymethyl polythiophene derivative.

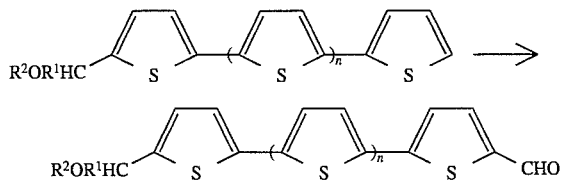

J. As shown in the following reaction, α-alkoxymethyl-α'''-acyl polythiophene can be obtained by the ordinal acylation of α-alkoxymethyl polythiophene.

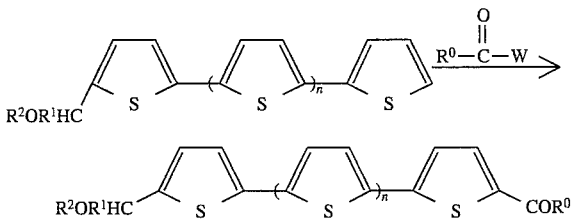

wherein W=halogen or OH; and
R°=$C_{1-4}$ alkyl.

Without further elaboration, it is believed that one skilled in the art can, based on the above description, utilize the present invention to its fullest extent. The following specific examples are, therefore, to be construed as merely illustrative, and not limitative of the remainder of the disclosure in any way whatsoever.

EXAMPLE 1

Synthesis of 5,5'-dihydroxymethyl bithiophene (a) 5-hydroxymethyl-5'-formyl bithiophene (0.2 g) was dissolved in ethanol (50 ml). $NaBH_4$ (0.1 g) was added at room temperature, and stirred for 1 hour. The solution was monitored by thin layer chromatography to determine whether the reaction was completed. $H_2O$ (50 ml) was added and the ethanol was removed under reduced pressure. After filtration, the solid product was recrystallized. The yield was almost quantitative and the melting point of the product was 158°–160° C.

Data of spectra:

$^1$H NMR ($D^6$-acetone) 7.03–6.87 (m, 4H, protons of thiophene) 4.73 (s, 4H, —$CH_2OH$)

IR (KBr) $cm^{-1}$ 3500–3300 (OH) 3050 2900, 2850 1453, 1415, 1360, 1230, 1200, 1175 1055, 1025, 1002 880, 870, 795

Mass spectrum, m/e (relative intensity) 226 ($M^+$, 100), 209 ($M^+$—OH, 73)

(b) 5-hydroxymethyl-5'-formyl bithiophene(0.6 g) was dissolved in tetrahydrofuran ("THF") (30 ml), $NaBH_4$ (0.16 g) was added, and the solution was stirred for 2 hours at room temperature. THF was removed under reduced pressure. The white solid obtained was washed with water and dried under reducing pressure. The yield was quantitative. The melting point of the product was 155°–156° C.

(c) 5-hydroxymethyl-5'-formyl bithiophene (0.5 g) was reduced in ethanol (75 ml) with $NaBH_4$ (0.3 g). The mixture was stirred for 3 hours at room temperature. The solution was concentrated and n-hexane was added to crystallize the white-powdered product. The crystal was filtered and washed with water. The crystal was dried by reducing the pressure and the yield was quantitative. The melting point of the product was 155°–156° C.

(d) 2-hydroxymethyl-5-iodothiophene was refluxed with Cu powder in dimethyl formamide ("DMF"). This Ullmann condensation also yielded a very low amount of 2,5-dihydroxymethyl bithiophene.

(e) The Ullmann condensation of 2-acetoxymethyl gave 5,5'-diacetoxymethylbithiophene. 5,5'-dihydroxymethyl bithiophene was obtained by alkaline hydrolysis and refined by column chromatography. The yield was about 20%.

EXAMPLE 2

Synthesis of 5,5'-diacetoxymethyl bithiophene 5,5'-dihydroxymethyl bithiophene (0.23 g), pyridine (1.2 ml) and acetic anhydride (0.3 ml) were mixed, stirred and kept overnight. Then the mixture was extracted with ethylacetate. The pyridine and acetic acid were removed by washing with weak base and weak acid, respectively. Silica gel powder was added into the ethyl acetate solution and the solvent was removed under reduced pressure. Coated silica gel powder was added to the silica gel column and chromatographed. The eluant was ethyl acetate/n-hexane (7/3). The white crystal thus obtained was further recrystallized with ethyl acetate/n-hexane mixture. The melting point of the product was 60° C.

Data of spectra:

IR $cm^{-1}$ 1725 (C=O)

Mass spectrum, m/e (relative intensity) 310 ($M^+$, 37) 251 ($M^+$—$CH_3CO_2$, 100) 192 ($M^+$-2 $CH_3CO_2$, 34)

EXAMPLE 3

Synthesis of 5-hydroxymethyl-5'-formyl bithiophene

Phosphorus oxychloride ("$POCl_3$") (1 ml) was added into DMF (20 ml) slowly under nitrogen gas atmosphere in ice bath and stirred for 1 hour. The DMF solution (5 ml) of 5-hydroxymethyl bithiophene (0.5 g) was dropped in slowly. The mixture was stirred for half an hour at room temperature, then the temperature was raised to 50° C. and was further stirred for 3 hours. The reaction solution was poured into potassium carbonate ice water solution. Then the solution was extracted with 100 ml of ethyl acetate. The extract was washed with water and dried over anhydrous magnesium sulfate. The solvent was removed under reduced pressure. The residual solid was purified by column chromatography. The eluant was ethyl acetate/n-hexane (3/7). The slightly yellowish product was recrystallized with ethyl acetate/n-hexane mixture. The melting point of the product was 123°–124° C. The yield was 85%.

Data of Spectra:

$^1$H NMR 400 MHz ($CDCl_3$), δ value 9.91 (s, 1H, —CHO) 7.73–7.02 (m, 4H, protons of thiophene) 4.91–4.90 (d, 2H, —$CH_2OH$)

IR (KBr) $cm^{-1}$ 3300 (OH) 1640 (C=O)

Mass spectrum, m/e (relative intensity) 224 ($M^+$, 100) 207 (M+—OH, 57) 195 (M+—CHO, 22)

EXAMPLE 4

Synthesis of 5-acetoxyethyl-5'-formyl bithiophene 5-hydroxymethyl-5'-formyl bithiophene (0.2 g) and pyridine (1 ml) were mixed together. Acetic anhydride (1 ml) was added slowly into the mixture while stirring. Ethylacetate (200 ml) and water (50 ml) were added 2 hours later. The ethyl acetate layer was washed with weak base, weak acid and water. The product was concentrated and purified by column chromatography. The eluant was ethyl acetate/n-hexane (1/9). Slightly yellowish crystal was obtained. The melting point of the crystal was 89°–91° C. The yield was 95%.

Data of Spectra:

$^1$H NMR 400 MHz ($CDCl_3$), δ value 9.83 (s, 1H, —CHO) 7.64–7.01 (m, 4H, protons of thiophene) 5.20 (s, 2H, —$CH_2OAc$) 2.08 (s, 3H, —$COCH_3$)

IR (KBr) $cm^{-1}$ 1740, 1660 (C=O)

EXAMPLE 5

Synthesis of 5-hydroxethyl-5"-formyl terthiophene $POCl_3$ (1 ml) was added to DMF (30 ml) slowly under nitrogen stream in ice bath condition. The solution was stirred for 1 hour and then DMF solution (20 ml) of 5-hydroxymethyl terthiophene (0.5 g) was dropped in slowly. The mixture was stirred for half an hour at room temperature and then the temperature was raised to 60° C. and stirred for further 2 hours. The reaction solution was poured into ice aqueous potassium carbonate solution. The solution was extracted with 300 ml of ethyl acetate and the extract was dehydrated with anhydrous magnesium sulfate. The solvent was removed under reduced pressure and the residual solid was purified by column chromatography. The eluant was ethyl acetate/n-hexane (3/7). The orange colored crystal was obtained and the melting point of the product was 176°–177° C. The yield was 80%.

Data of Spectra:

$^1$H NMR 400 MHz ($CDCl_3$), δ value 9.86 (s, 1H, —CHO) 7.65–6.91 (m, 6H, protons of thiophene) 4.80 (s, 2H, —$CH_2OH$)

IR (KBr) $cm^{-1}$ 3400 (OH) 1660 (C=O)

Mass spectrum, m/e (relative intensity) 306 ($M^+$, 100) 289 ($M^+$—OH, 56)

EXAMPLE 6

Synthesis of 5,5"-dihydroxymethyl terthiophene 5,5'-diformyl terthiophene (0.6 g) was added into THF (30 ml). The temperature was raised to 50° C. until the solute was completely dissolved, then $NaBH_4$ (0.25 g) was added and stirred for 3 hours at 50° C. The solvent was removed under reduced pressure. Ethylacetate and water were added to dissolve the residual solid. The ethyl acetate layer was washed with water and dried over anhydrous magnesium sulfate. The ethyl acetate layer was filtered and concentrated to obtain slightly yellowish solid (0.95 g). This was recrystallized from alcohol and the melting point of the product was 182°–183° C.

Data of Spectra:

$^1$H NMR 400 MHz ($CDCl_3$), δ value 7.04–6.89 (m, 6H, protons of thiophene) 4.79 (d, 4H, $CH_2$ OH) 1.51 (br. s., OH)

Mass spectrum, m/e (relative intensity) 308 ($M^+$, 58) 306 ($M^+$-2H, 100)

EXAMPLE 7

Synthesis of 5-hydroxymethyl-5"-(1-hydroxypropyl) terthiophene 5-hydroxymethyl-5"-formyl terthiophene (0.5 g) was dissolved into anhydrous THF (50 ml). A little excess of calculated amount of 2.0M ethyl magnesium bromide were added to the THF solution under nitrogen atmosphere. The solution was stirred for 3 hours at room temperature. Aqueous ammonium chloride solution was added to hydrolyze the above reaction solution to obtain the product. The product is collected, separated and purified by column chromatography. The eluant was ethyl acetate/n-hexane (3/7) solution and concentrated to obtain orange powdered solid (0.3 g). The melting point was 131°–132° C.

Data of spectra:

$^1$H NMR 400MHz (CDCl$_3$), δ value 7.03–6.85 (m, 6H, protons of thiophene) 4.79–4.78 (m, 3H, —CH$_2$OH and

1.91–1.77 (m, 2H, —CH$_2$CH$_3$) 0.99–0.95 (t, 3H, —CH$_3$)
IR (KBr) cm$^{-1}$ 3400 (OH), 2900 (saturated CH)

EXAMPLE 8

Synthesis of 5-succinoyloxethyl-5'-formyl bithiophene 5-hydroxymethyl-5'-formyl bithiophene (0.63 g), pyridine (10 ml) and succinyl anhydride (0.12 g) were mixed together. The mixture was stirred at 40° C. Thin layer chromatography was applied to monitor the reaction. After the reaction was completed, diluted hydrochloric acid and ethyl acetate were added. The ethyl acetate solution was washed with water to remove pyridine completely. Then the ethyl acetate layer was dehydrated with anhydrous magnesium sulfate and filtered through silica gel layer. After removal of the solvent and the product was recrystallized with ethyl acetate/n-hexane to give a slightly yellowish crystal (0.6 g). The melting point was 127° C.

Data of spectra:

$^1$H NMR 400MHz (CDCl$_3$), δ value 9.84 (s, 1H, —CHO) 7.65–7.02 (m, 4H, protons of thiophene) 5.25 (s, 2H, —CHO—) 2.72–2.64 (m, 4H, —COCH$_2$CH$_2$CO—) 2.40 (br, OH)
IR (KBr) cm$^{-1}$ 3200–2500 (OH) 1730, 1705, 1650 (C=O)

EXAMPLE 9

Synthesis of 5,5'-disuccinoyloxymethyl bithiophene 5,5'-dihydroxymethyl bithiophene (0.5 g), pyridine (10 ml) and succinyl anhydride (2 g) were mixed together. The mixture was stirred at 40° C. Thin layer chromatography was applied to monitor the reaction. After the reaction was completed, ethyl acetate was added to extract the product. The ethyl acetate layer was washed with diluted hydrochloric acid and water in order to remove pyridine completely. The product was filtered through silica gel powder layer and recrystallized with ethyl acetate/n-hexane. White crystal (0.45 g) was obtained. The melting point of the crystal was 137° C.

Data of spectra:

$^1$H NMR 400MHz (CDCl$_3$), δ value 7.00–6.90 (m, 4H, protons of thiophene) 5.28–5.23 (m, 4H, —CH$_2$O—) 4.78–4.75 (m, 4H, —CH$_2$O—) 2.69–2.64 (m, 8H, —CO—CH$_2$CH$_2$—CO—)
IR (KBr) cm$^{-1}$ 3600–2500 (OH) 1718, 1688 (C=O)

EXAMPLE 10

Synthesis of 5-ethoxymethyl terthiophene 5-formyl terthiophene (0.3 g) was dissolved in ethanol (10 ml) by stirring at room temperature. To the solution, 0.04 g of NaBH$_4$ was slowly added. After the solution became clear in about 20 minutes, diluted hydrochloric acid was slowly added until bubbling stopped. The stirring was continued for about 2 hours, followed by chloroform extraction and silica gel column chromatography (eluted by ethyl acetate/n-hexane=1/19). The product was recrystallized with chloroform/ethyl acetate mixture to give a slightly yellowish crystal (melting point 76°–77° C.). The yield was about 41%.

The yield could be increased to 85% or higher by substituting absolute ethanol for alcohol and concentrated hydrochloric acid for diluted hydrochloric acid. More specifically, 5-formyl terthiophene (0.2 g) was first dissolved in absolute ethanol (15 ml) at room temperature. To the solution, 0.03 ml concentrated hydrochloric acid/absolute ethanol mixture (0.3 ml conc. HCl in 10 ml absolute ethanol) was then added. After stirring for 2 hours, 0.8 g sodium bicarbonate (NaHCO$_3$) was added and the stirring was continued for 0.5 hours followed by filtration. The ethanol was removed under reduced pressure. 5-ethoxymethyl terthiophene thus obtained was purified by silica gel chromatography.

Data of spectra:

$^1$H NMR 400MHz (CDCl$_3$), δ value 7.20–6.87 (m, 7H, protons of thiophene) 4,62 (s, 2H, —CH$_2$OC$_2$H$_5$) 3.55 (q, 2H, —CH$_2$OCH$_2$CH$_3$) 1.25 (t, 3H, —OCH$_2$CH$_3$)
IR (KBr) cm$^{-1}$ 3050 (aromatic CH) 2971, 2852 (saturated CH) 1091 (—C—O—)
Mass spectrum, m/e (relative intensity) 306 (M$^+$, 100) 261 (M$^+$—OC$_2$H$_5$, 33)

BIOLOGICAL ACTIVITY

The anti-edema activity was tested according to the conventional toe edema method using carrageenan as pyrogen and indomethacin as control inhibitory agent. See C. A. Winter, E. A. Risley and G. W. Nuss, Biol. Med., 111, 544 (1962); and A. P. Roszkowshi, W. H. Rooks II, A. J. Tomolonis and L. M. Miller, J. Pharmacol. Exp. Ther., 179, 114 (1971), both of which are hereby incorporated by reference.

In general, polythiophene derivatives of this invention have shown significant anti-edema activity. For example, the anti-edema effect of dihydroxymethylbithiophene and its diacetate is shown in the Table 1.

TABLE 1

Anti-edema Effect of Polythiophene Derivatives*

| Compound | Dosage (mg/kg) | Inhibition rate (%) |
|---|---|---|
| HOH$_2$C-[thiophene]$_2$-CH$_2$OH | 10 | 26 |
|  | 50 | 34 |
|  | 100 | 37 |
|  | 200 | 41 |
| AcOH$_2$C-[thiophene]$_2$-CH$_2$OAc | 50 | 17 |
|  | 100 | 28 |
|  | 200 | 28 |
| ([thiophene]$_2$-C≡CCH$_2$CH$_2$OH) | 50 | 32 |
|  | 100 | 36 |
|  | 200 | 38 |

*A compound with an inhibition rate above 30% is considered to be also anti-inflammatory.

OTHER EMBODIMENTS

From the above description, one skilled in the art can easily ascertain the essential characteristics of the present invention, and without departing from the spirit and scope thereof, can make various changes and modifications of the invention to adapt it to various usages and conditions.

For example, a pharmaceutical composition comprising one or more the above-described polythiophene derivatives is also within the scope of the present invention. Thus, other embodiments are also within the claims.

What is claimed is:

1. A compound of the formula:

$$R-[thiophene]-[thiophene]_n-[thiophene]-CH(R^1)COR^4$$

in which n is 0;

R is —CH(R$^1$)OCH$_3$, —CH(R$^1$).OR$^2$, CH(R$^1$).O(C$_2$-C$_6$ alkyl), —CH(O—Z)$_2$, or —COR$^3$;

R$^1$ is H, C$_{1-6}$ alkyl, C$_{2-6}$ alkenyl, C$_{1-6}$ alkoxy, or C$_{1-6}$ acyloxy;

each R$^2$ and R$^4$, independently, is H, C$_{2-6}$ alkenyl, C$_{1-6}$ hydroxyalkyl, C$_{2-6}$ alkoxyalkyl, tetrahydropyranyl, or —CO—Y—COOH; and R$^3$ is H, C$_{1-6}$ alkyl, C$_{2-6}$ alkenyl, or C$_{1-6}$ alkoxy; wherein Z is C$_{1-6}$ alkyl, C$_{2-6}$ alkenyl, or C$_{1-6}$ acyl; and Y is C$_{1-6}$ alkylidene, C$_{2-6}$ alkenylidene, or phenylene provided that R and —CH(R$^1$).OR$^4$ cannot both be CH2OH and further provided that when R is CHO, —CH(R$^1$).OR$^4$ cannot be CH2OH; or a salt or an ester thereof.

2. The compound of claim 1, wherein R is —CH(R$^1$).OR$^4$ or —COR$^3$; each R$^2$ and R$^4$, independently, is H, or —CO—Y—COOH; and Y is —CH$_2$—CH$_2$—, —CH=CH—, or phenylene.

3. The compound of claim 2, wherein R is —CH(R$^1$).OR$^4$ and each R$^2$ and R$^4$, independently, is H.

4. The compound of claim 2, wherein R is —CH(R$^1$).OR$^2$ and each R$^2$ and R$^4$, independently, is —CO—Y—COOH.

5. The compound of claim 2, wherein R is —COR$^3$ and each R$^2$ and R$^4$, independently, is C$_{1-6}$ acyl or —CO—Y—COOH.

6. The compound of claim 1 of the following formula:

OHC-[thiophene]-[thiophene]-CH$_2$OCCH$_2$CH$_2$COOH,

OHC-[thiophene]-[thiophene]-CH$_2$OC-[phenyl]-COOH,

H$_3$CCOH$_2$C-[thiophene]-[thiophene]-CH$_2$OCCH$_3$,

HOOCCH$_2$CH$_2$COH$_2$C-[thiophene],

-[thiophene]-CH$_2$OCCH$_2$CH$_2$COOH,

OHC-[thiophene]-[thiophene]-CH$_2$OCCH$_2$CH$_2$COOH,

HOOCCH$_2$COH$_2$C-[thiophene]-[thiophene]-CH$_2$OCCH=CHCOOH,

OHC-[thiophene]-[thiophene]-CH$_2$OCCH=CHCOOH, or

HOOC-[phenyl]-COH$_2$C-[thiophene]-,

-[thiophene]-CH$_2$OC-[phenyl]-COOH.

* * * * *